US010927055B2

(12) United States Patent
Al-Kinany et al.

(10) Patent No.: US 10,927,055 B2
(45) Date of Patent: Feb. 23, 2021

(54) METHOD OF PREPARING A MODIFIED ZEOLITE CATALYST AND PREPARING ETHYLBENZENE USING ONE CYCLE PROCESS

(71) Applicants: The King Abdulaziz City for Science and Technology, Riyadh (SA); Inorganic Chemistry Laboratory Oxford University, Oxford (GB)

(72) Inventors: Mohammad C. Al-Kinany, Riyadh (SA); Hamid A Almegren, Riyadh (SA); Saud A Aldrees, Riyadh (SA); Eyad Al-Ghilan, Riyadh (SA); Sami Al-Dress, Riyadh (SA); Abdullah Al-Ghamdi, Riyadh (SA); Peter P Edwards, Oxford (GB); Tiancun Xiao, Oxford (GB)

(73) Assignees: THE CHANCELLOR, MASTERS AND SCHOLARS OF THE UNIVERSITY OF OXFORD, Oxford (GB); THE KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 0 days.

(21) Appl. No.: 15/046,296

(22) Filed: Feb. 17, 2016

(65) Prior Publication Data

US 2017/0233308 A1    Aug. 17, 2017

(51) Int. Cl.
| C07C 2/66 | (2006.01) |
| C07C 2/64 | (2006.01) |
| C07C 2/54 | (2006.01) |
| B01J 29/06 | (2006.01) |
| B01J 37/34 | (2006.01) |

(Continued)

(52) U.S. Cl.
CPC ............... *C07C 2/66* (2013.01); *B01J 29/06* (2013.01); *B01J 29/405* (2013.01); *B01J 37/08* (2013.01); *B01J 37/12* (2013.01); *B01J 37/14* (2013.01); *B01J 37/343* (2013.01); *C07C 2529/06* (2013.01)

(58) Field of Classification Search
CPC .... C07C 2/76; C07C 2/64; C07C 2/54; C07C 2/66; C07C 2/68
See application file for complete search history.

(56) References Cited

U.S. PATENT DOCUMENTS

| 5,157,185 | A | * | 10/1992 | Chu | ......................... B01J 29/40 502/71 |
| 5,227,558 | A | * | 7/1993 | Shamshoum | ............. C07C 2/66 585/446 |
| 8,283,273 | B2 | * | 10/2012 | Kelly | ..................... B01J 29/061 502/60 |

* cited by examiner

*Primary Examiner* — Youngsul Jeong
(74) *Attorney, Agent, or Firm* — Dennemeyer & Associates, LLC; Steven M. Shape

(57) ABSTRACT

The invention provides a modified zeolite, a method of preparing the modified zeolite and a method of one cycle alkylating benzene in presence of one of an unmodified and modified zeolite catalyst. The modified zeolite catalyst includes zeolite with ratio of silica to alumina ranging between 5% to 95% of silica and 95% to 5% alumina, kaolinite and a binder, wherein the zeolite is modified with one or more metal oxides of Lanthanide-series of the Periodic Table. The method of alkylating benzene is one cycle process in presence of a catalyst that includes charging benzene and ethylene gas feedstock to an alkylation zone. Heated benzene and the ethylene gas feedstock are contacted in a fixed bed reactor in the alkylation zone. The catalyst for alkylating benzene is added in a catalyst zone of the fixed bed reactor.

5 Claims, 2 Drawing Sheets

(51) Int. Cl.
*B01J 37/08* (2006.01)
*B01J 37/12* (2006.01)
*B01J 29/40* (2006.01)
*B01J 37/14* (2006.01)

METHOD OF PREPARING A MODIFIED ZEOLITE CATALYST AND PREPARING ETHYLBENZENE USING ONE CYCLE PROCESS

FIELD OF THE INVENTION

The invention generally relates to field of preparation of modified zeolite catalyst and ethylbenzene by one cycle process. More specifically, the invention relates to a method of preparing ethylbenzene using modified zeolite catalysts.

BACKGROUND OF THE INVENTION

Generally, ethylbenzene is important as an intermediate in petrochemical industries. Ethylbenzene is typically formed by one or more aromatic conversion processes involving alkylation of benzene. In industry, ethylbenzene is mainly manufactured by the alkylation of benzene with ethylene via two processes, i.e. the liquid-phase process and gas-phase process. Currently, ethylbenzene is prepared using liquid phase alkylation in the presence of aluminum chloride ($AlCl_3$) as a catalyst. However, the liquid phase alkylation; the current technique being used to prepare ethylbenzene either gives low yield, leads to environmental impact, uses corrosive catalysts, and forms oligomers and other impurities. Most catalysts used in the alkylation of benzene are strong mineral acids or Lewis acids, and such catalysts are highly toxic, corrosive, capable of corroding storage and disposal containers. The final product of the alkylation process requires an additional step of separating acids. The additional step of separating acids includes difficult and energy consuming process. Due to the partial release of the acids, corrosion cannot be avoided completely. Such catalysts are also not active for polyethylbenzene transalkylation and cannot be regenerated.

Zeolite became a substitution for aluminum chloride catalyst in industries for preparing ethylbenzene using ethylene and benzene. Typically, liquid benzene and ethylene gas are charged into an alkylation zone containing one or more reactors. The one or more reactors contain an alkylation catalyst to produce ethylbenzene in gas phase. However, polyethylated benzenes such as diethylbenzene and triethylbenzene isomers are formed rather than the desired ethylbenzene. In order to minimize the production of polyethylated products of benzene partially, the molar ratio of benzene to ethylene is maintained at a range of about 3:1 to about 16:1 throughout the alkylation zone. However, a transalkylation reactor is required to be employed to convert the polyethylated benzenes into ethylbenzene, which is requires additional step, cost and time.

Generally, the gas phase process is carried out under moderate pressure [1.0 megapascal (Mpa)-20.8 Mpa] and high temperature [300 degree Celsius (° C.)-500° C.], which leads to higher energy consumption, requires more cooling systems and strict requirements for an apparatus. When ZSM-5 based catalyst is used for preparing ethylbenzene using ethylene and benzene, more byproducts are produced, especially toluene at about 1000-1200 parts-per-million (ppm). The amount of toluene produced is much higher than the levels required by a downstream process. The selectivity of ZSM-5 based catalyst towards ethylbenzene is low. The ZSM-5 based catalyst also deactivates and requires periodic regeneration.

Thus, there is need for a more efficient, safe and environmental friendly catalysts for alkylation of benzene to produce ethylbenzene.

BRIEF DESCRIPTION OF THE FIGURES

The accompanying figures together with the detailed description below forms part of the specification and serves to further illustrate various embodiments and to explain various principles and advantages all in accordance with the invention.

DETAILED DESCRIPTION OF THE INVENTION

Figure 1:
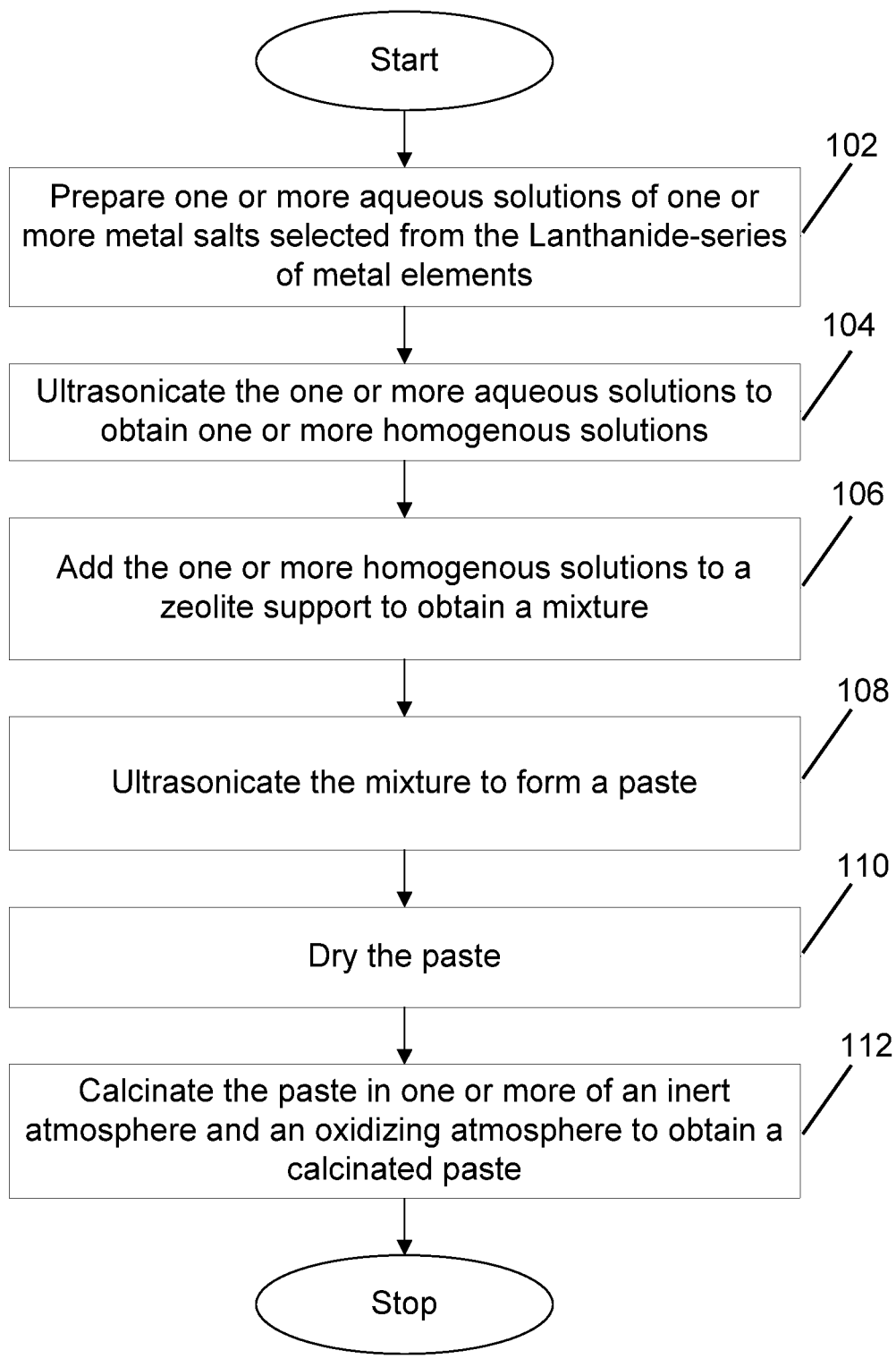
FIG. 1 illustrates a flow diagram of a method of preparing a modified zeolite catalyst in accordance with the embodiments of the invention.

Before describing in detail embodiments that are in accordance with the invention, it should be observed that the embodiments reside primarily in a method of preparing a modified zeolite catalyst and a method of preparing ethylbenzene in one cycle process using a zeolite catalyst.

In this document, terms "comprises," "comprising," or any other variation thereof, are intended to cover a non-exclusive inclusion, such that a process, method, or composition that comprises a list of elements does not include only those elements but may include other elements not expressly listed or inherent to such process, method, or composition. An element proceeded by "comprises . . . a" does not, without more constraints, preclude the existence of additional identical elements in the process, method, or composition that comprises the element.

Generally speaking, pursuant to various embodiments, the invention provides a modified zeolite catalyst that includes zeolite with ratio of silica to alumina ranging between 5% to 95% of silica and 95% to 5% alumina, kaolinite and a binder, wherein the zeolite is modified with one or more metal oxides of Lanthanide-series of the Periodic Table. In an embodiment, the weight ratio of zeolite/kaolinite/binder in the modified zeolite catalyst is about 10/25/65 to about 60/5/35.

Binder materials include synthetic or naturally occurring substances as well as inorganic materials such as, but not limited to, clay, silica and metal oxides. Naturally occurring clays, which can be composited with inorganic oxide materials, include montmorillonite and kaolin families. The montmorillonite and kaolin families include subbentonites and kaolins. The clays or others in which the main mineral constituent is halloysite, kaolinite, dicknite, nacrite, or anauxite, can be used in the raw state as originally mined or initially subjected to calcination, acid treatment, or chemical modification. The binder is selected from a group of kaolin, silica, alumina, zirconia, titania, silica-alumina, silica-magnesia, silica-zirconia, silica-titania, silica-alumina-zirconia, silica-alumina-magnesia, silica-magnesia-zirconia. The weight percentage (wt %) of the binder in the modified zeolite catalyst is about 0.5 wt % to 65 wt %.

The atomic numbers of the one or more metal oxides of the Lanthanide series in the modified zeolite catalyst is 57-71. The weight percentage of the one or more metal oxides in the modified zeolite catalyst is less than 35 wt %. When the zeolite is modified with one metal oxide of Lanthanide-series of the Periodic Table, then the metal oxide is about 0.1 wt % to about 25 wt %. When the zeolite is modified with two metal oxides of Lanthanide-series of the Periodic Table, then the two metal oxides are about 0.1 wt % to about 35 wt %.

The invention also provides a method of preparing the modified zeolite catalyst that includes preparing one or more aqueous solutions of one or more metal salts selected from the Lanthanide-series of metal elements. The one or more aqueous solutions are ultrasonicated to obtain one or more homogenous solutions. The one or more homogenous solutions are added to a zeolite support to obtain a mixture. Thereafter, the mixture is ultrasonicated to form a paste and the paste is allowed to dry. Finally, the paste calcinated in one or more of an inert atmosphere and an oxidizing atmosphere to obtain a calcinated paste.

The invention also provides a method of alkylating benzene by one cycle process in presence of a catalyst that includes charging benzene and ethylene gas feedstock to an alkylation zone. Heated benzene and the ethylene gas feedstock are contacted in a fixed bed reactor in the alkylation zone. The catalyst for alkylating benzene is added in a catalyst zone of the fixed bed reactor. The arrangement of the fixed bed reactor is such that the method of alkylating benzene is one cycle process. The catalyst is one of an unmodified zeolite catalyst and the modified zeolite catalyst. The unmodified zeolite catalyst includes zeolite with ratio of silica to alumina ranging between 20% to 80% of silica and 80% to 20% alumina and a binder. The modified zeolite catalyst includes zeolite with ratio of silica to alumina ranging between 5% to 95% of silica and 95% to 5% alumina, kaolinite and a binder, wherein the zeolite is modified with one or more metal oxides of Lanthanide-series of the Periodic Table. In an embodiment, the unmodified zeolite catalyst includes 15% of binder ($Al_2O_3$), 30% Zeolite with ratio of silica to alumina 28, and 55% of kaolinite.

FIG. 1 illustrates a flow diagram of a method for preparing a modified zeolite catalyst.

At step 102, one or more aqueous solutions of one or more metal salts selected from the Lanthanide-series of metal elements are prepared. The one or more metal salts are selected from a group consisting of, but not limited to, acetate hydrate, chloride anhydrous, chloride heptahydrate, chloride hydrate, nitrate hexahydrate, nitrate pentahydrate, acetylacetonate, fluoride or octanoate. The one or more aqueous solutions of the one or more metal salts are prepared at a temperature of about 25° C. to about 80° C.

At step 104, the one or more aqueous solutions are ultrasonicated to obtain one or more homogenous solutions. In an embodiment, the one or more aqueous solutions of the one or more metal salts are ultrasonicated at a temperature of about 25° C. to about 80° C. for a period of about 1 hour to about 3 hours.

At step 106, the one or more homogenous solutions are added to a dried zeolite support to obtain a mixture. The zeolite support is unmodified zeolite catalyst. The unmodified zeolite catalyst includes zeolite with ratio of silica to alumina ranging between 20% to 80% of silica and 80% to 20% alumina and a binder.

Thereafter, at step 108, the mixture is ultrasonicated to form a paste. In an embodiment, the mixture is ultrasonicated for a period of about 1 hour to about 10 hours to form the paste.

At step 110, the paste is allowed to dry. The paste is dried at a temperature below 100° C. under vacuum. In a preferred embodiment, the paste is dried at a temperature of about 80° C. to about 90° C. under vacuum, for a sufficient time period to remove water completely.

Finally, at step 112, the paste is calcinated in one or more of an inert atmosphere and an oxidizing atmosphere to obtain a calcinated paste.

In an embodiment, the paste is calcinated in the inert atmosphere at a temperature of about 250° C. to about 600° C. for a period of about 1 hour. In a preferred embodiment, the paste is calcinated in the inert atmosphere at a temperature of about 350° C. to about 550° C. for a period of about 1 hour. The inert atmosphere includes helium. The paste is calcinated at a programmable temperature of about 2° C. per minute to about 10° C. per minute with a flow rate of helium ranging between 0.5 milliliter per minute (ml/min) and 10 ml/min.

In another embodiment, the paste is calcinated in the oxidizing atmosphere at a temperature of about 250° C. to about 600° C. for a period of about 2 hours to about 12 hours. In a preferred embodiment, the paste is calcinated in the oxidizing atmosphere at a temperature of about 350° C. to about 550° C. for a period of about 2 hours to about 12 hours. The oxidizing atmosphere comprises oxidizing agents such as, but not limited to, oxygen and air. The paste is calcinated at a programmable temperature of about 2° C. per minute to about 10° C. per minute with a flow rate of the oxidizing agents ranging between 0.5 ml/min and 50 ml/min.

Optionally, the calcinated paste is ultrasonicated under dry conditions. In an embodiment, the calcinated paste is ultrasonicated under dry conditions at a temperature of about 25° C. to about 60° C. The preferred temperature for ultrasonicating the calcinated paste under dry conditions is about 40° C.

The modified zeolite catalyst is characterized by a Brunauer, Emmett and Teller (BET) surface area ranging between 232 meter square per gram ($m^2/g$) and 242 $m^2/g$; a pore volume ranging between 0.183 centimeter cube per gram ($cm^3/g$) and 0.152 $cm^3/g$; and a pore size ranging between 35.4 Angstrom (Å) to 34.2 Å

Figure 2:
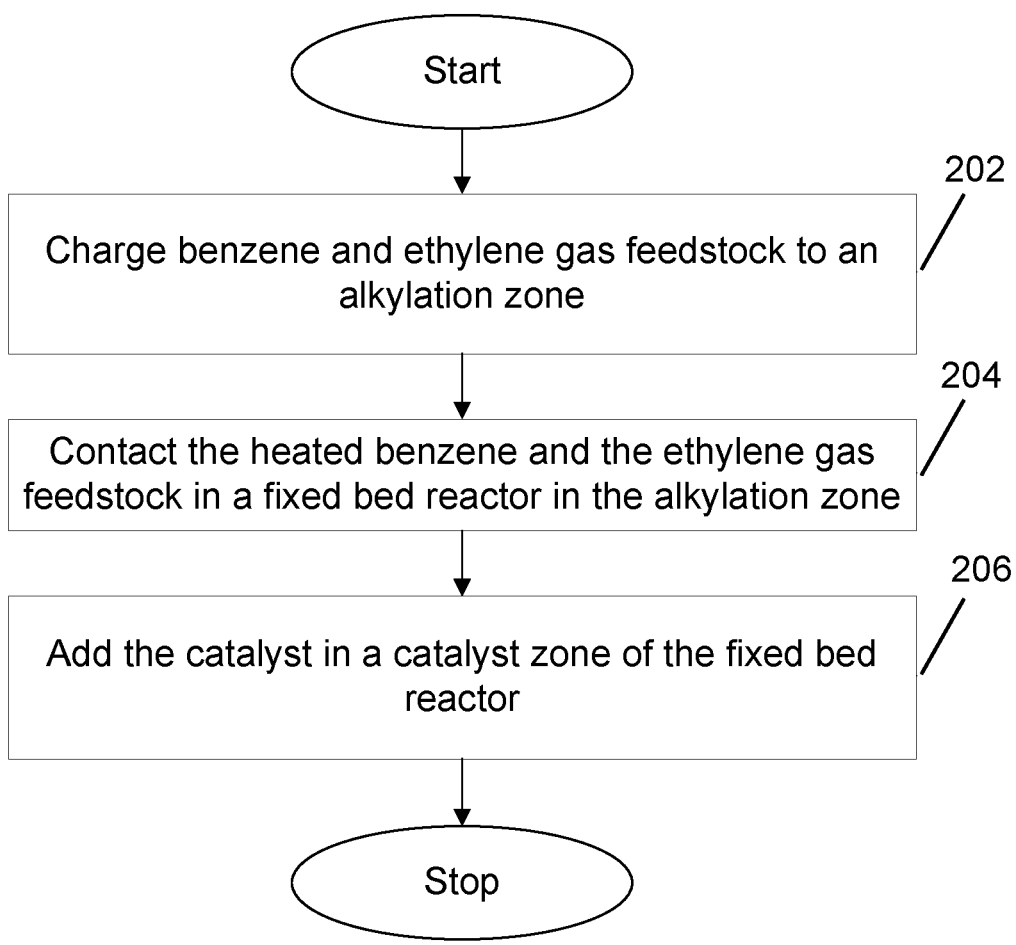
FIG. 2 illustrates a flow diagram of a method of alkylating benzene in presence of a catalyst in one cycle process in accordance with the embodiments of the invention.

FIG. 2 illustrates a flow diagram of a method of alkylating benzene by one cycle process in presence of a catalyst. At step 202, benzene and ethylene gas feedstock is charged to an alkylation zone. The molar ratio of benzene to ethylene is about 1:6 to about 15:1. In a preferred embodiment, the molar ratio of benzene to ethylene is about 1:1 to about 10:1. The benzene and ethylene are completely in the gas phase and are highly pure which means free from moisture, sulfur compounds, any kind of other gases, or dilution with other material.

At step 204, pre-heated benzene and the ethylene gas feedstock are contacted in a fixed bed reactor in the alkylation zone. The fixed bed reactor can be a fixed bed down pass flow stainless steel reactor. The arrangement of the fixed bed reactor is such that the method of alkylating benzene is one cycle process. In an embodiment, a stream of preheated mixture of benzene and ethylene gas at a temperature ranges between 90° C. to 250° C., preferably 100° C. to 200° C., is fed in the fixed bed reactor.

At step 206, the catalyst for alkylating benzene is added in a catalyst zone of the fixed bed reactor. The catalyst is one of unmodified zeolite and modified zeolite catalyst. The unmodified zeolite catalyst includes zeolite with ratio of silica to alumina ranging between 20 wt % to 80 wt % of silica and 80 wt % to 20 wt alumina and a binder. The modified zeolite catalyst includes zeolite with ratio of silica to alumina ranging between 5 wt % to 95 wt % of silica and 95 wt. % to 5 wt % alumina, kaolinite and a binder, wherein the zeolite is modified with one or more metal oxides of Lanthanide-series of the Periodic Table.

In an embodiment, the alkylation of benzene is carried out under pressure ranging between about 1.0 bar and about 20 bar. In a preferred embodiment, the alkylation of benzene is carried out under pressure ranging between about 1.0 bar and about 10 bar. A feed weight hourly space velocity (WHSV) based on ethylene is from about 0.1 per hour ($hr^{-1}$) to about 400 $hr^{-1}$. In a preferred embodiment, the feed WHSV based on ethylene is from about 0.5 $hr^{-1}$ to about 150 $hr^-$.

In an embodiment, the alkylation of benzene is carried out at a temperature of about 100° C. to 500° C. In a preferred embodiment, the alkylation is carried out under out at a temperature of about 200° C. to about 450° C.

The alkylation of benzene is carried out in a continuous gas phase using the fixed bed reactor in a bench top pilot plant. In an embodiment, the alkylation of benzene is carried out in the continuous gas phase using the fixed bed reactor in the bench top pilot plant in presence of an inert gas as a diluent. The diluent of the inert gas is one or more of Nitrogen, Helium and Argon; and the diluent has a flow rate of less than 4.5 ml/min.

In an embodiment, the bench top pilot plant is a one cycle pilot plant fitted with mass flow meters and a fixed bed reactor placed in a cylindrical furnace equipped with a coaxial thermocouple. The inside diameter and a length of a fixed bed reactor is 8 mm and 300 mm. The catalyst zone is in the middle of the fixed bed reactor and the catalyst zone is filled with 0.5 grams to 1.0 grams of the catalyst diluted with an equal amount of quartz particles in order to minimize temperature gradient. The catalyst zone is about 30 millimeter (mm) in size. The quartz particles are 100 to 600 meshes. In the center of a catalyst zone, a thermocouple is installed so that the thermocouple is in contact with catalyst particles to measure reaction temperature. The heating zones at an inlet and an outlet of the fixed bed reactor are also measured with the thermocouple located inside a furnace and a temperature controller controls the heating zones. A ceramic is also placed in the empty space in the fixed bed reactor to improve the heat exchange and mixing between benzene and ethylene.

Preparation of a Modified Zeolite Catalyst with One Transition Metal Oxide

Working Example 1

In this working example, the modified zeolite catalyst is prepared with Lanthanum (III). An aqueous solution is prepared by dissolving 0.5 g to 30 g of Lanthanum (III) acetate hydrate, Lanthanum (III) chloride anhydrous, Lanthanum (III) chloride heptahydrate, Lanthanum (III) chloride hydrate, Lanthanum (III) nitrate hexahydrate, Lanthanum (III) nitrate pentahydrate, Lanthanum (III) acetylacetonate, Lanthanum (III) fluoride, or Lanthanum (III) octanoate at room temperature in 100 milliliter (ml) of deionized water. The aqueous solution is stirred at room temperature for 60 minutes. Thereafter, the aqueous solution is stirred at 50° C. for a period of 2 hours until a clear solution is obtained. The clear solution is filtered and ultrasonicated for 60 minutes. The heated and ultrasonicated clear solution is added to 1.0 g to 80 g of unmodified zeolite catalyst. The resultant mixture is stirred for 60 minutes and ultrasonicated for a period of 12 hours at a temperature of about 30° C. to about 50° C. until a homogenous mixture is obtained. The homogenous mixture is dried using a rotatory evaporator under vacuum at a temperature of 80° C. to 90° C. Thereafter, the homogenous mixture is dried in a programmable oven under vacuum at a temperature ranging from 25° C. to 95° C. The homogenous mixture is calcinated at a temperature of 250° C. to 600° C. first in helium for 1 hour and thereafter in air or oxygen for 12 hours. The preferable temperature for calcination of the homogenous mixture is 350° C. to 550° C. Finally, the modified zeolite catalyst formed is ultrasonicated under dry condition for a period of 3 hours.

Preparation of Modified Zeolite Catalyst with Two Transition Metal Oxides

Working Example 2

In this working example, the modified zeolite catalyst is prepared with Lanthanum and Cerium oxides. An aqueous solution (A) is prepared by dissolving 0.5 g to 30 g of Lanthanum (III) acetate hydrate, Lanthanum (III) chloride anhydrous, Lanthanum (III) chloride heptahydrate, Lanthanum (III) chloride hydrate, Lanthanum (III) nitrate hexahydrate, Lanthanum (III) nitrate pentahydrate, Lanthanum (III) acetylacetonate, Lanthanum (III) fluoride, or Lanthanum (III) octanoate at room temperature in 100 milliliter (ml) of deionized water. Aqueous solution (A) is stirred at room temperature for 60 minutes. Thereafter, aqueous solution (A) is stirred at 50° C. for a period of 2 hours until a clear solution (A) is obtained. Clear solution (A) is filtered and ultrasonicated for 60 minutes. An aqueous solution (B) is prepared by dissolving 0.25 g to 15 g of Cerium (III) nitrate hexahydrate, Cerium (III) acetate hydrate, Cerium (III) hydroxide, Cerium (III) bromide, Cerium (III) fluoride trihydrate, Cerium (IV) ammonium nitrate, Cerium (IV) nitrate, Cerium (IV) ammonium sulphate, or Cerium (IV) ammonium phosphate at room temperature in 100 milliliter (ml) of deionized water. Aqueous solution (B) is stirred at room temperature for 60 minutes. Thereafter, aqueous solution (B) is stirred at 50° C. for a period of 2 hours until a clear solution (B) is obtained. Clear solution (B) is filtered and ultrasonicated for 60 minutes.

The two clear solutions (A) and (B) are combined to form a mixture. The mixture is stirred at a temperature of 50° C. for a period of 2 hours until a homogenous solution is obtained. The homogenous solution is ultrasonicated for a period of 3 hours at a temperature of 80° C. The heated and ultrasonicated homogenous solution is added to 1.0 g to 40.0 g of unmodified zeolite catalyst. The resultant mixture is stirred for 60 minutes and ultrasonicated for 12 hours at a temperature of 30° C. to 50° C. until a homogenous mixture is obtained. The homogenous mixture is dried using a rotatory evaporator under vacuum at a temperature of 70° C. to 90° C. Thereafter, the homogenous mixture is dried in a programmable oven under vacuum at a temperature ranging from 25° C. to 95° C. The homogenous mixture is calcinated at a temperature of 250° C. to 600° C. first in helium for 1 hour and thereafter, in air or oxygen for 12 hours. The preferable temperature for calcination of the homogenous mixture is 350° C. to 550° C. Finally, the modified zeolite catalyst formed is ultrasonicated under dry condition for a period of 3 hours.

One Cycle Ethylation of Benzene Process

Working Example 3

In this working example, three catalysts which are catalyst 1, catalyst 2 and catalyst 3 are used for one cycle ethylation of benzene with ethylene under variable conditions of temperatures, benzene to ethylene ratios and space velocities, without recycling the byproducts to a reactor and/or a transalkylator for transalkylation, isomerization or disproportionation reactions. Catalyst 1 is unmodified zeolite catalyst, catalyst 2 is zeolite catalyst after modification with Lanthanum oxide, and catalyst 3 is zeolite catalyst after modification with Lanthanum oxide and Cerium oxide.

Typically, the ethylation of benzene process is carried out in one cycle gas phase continuous process, wherein benzene and ethylene are processed in a down flow fixed bed tube reactor (reactor) over unmodified or modified zeolite catalyst with metal oxides.

The middle of the reactor is loaded with 0.5 g to 10 g of unmodified or modified zeolite catalyst. A feedstock of the ethylation reaction consisting of benzene and ethylene is introduced at the top of the reactor. Normally, the flow rate of ethylene is between 2.0 to 22 ml/min with benzene to ethylene mole ratios ranging from 1:6 to 15:1. The preferred mole ratio of benzene to ethylene is ranging from 1:1 to 10:1. The flow rate of ethylene is adjusted through a separate thermal mass flow controller (Bronkhorst). The flow rate of benzene is controlled through a one channel syringe pump (Cole-Parmer). The gas phase process is performed at temperatures ranging from 100° C. to 500° C. The preferred temperature range for the gas phase process is 200° C. to 450° C. The reaction pressure can vary depending on the mole ratios of the feed employed. The process is performed at a pressure ranging from 1.0 bar to 20 bar. The preferred pressure range is from 1.0 bar to 10 bar. The contact time required for the reaction depends on the feed and reaction conditions. The WHSV range of 0.1 $hr^{-1}$ to 400 $hr^{-1}$ can be employed, but WHSV of 0.5 $hr^{-1}$ to 150 $hr^{-1}$ is preferred. Products of ethylation reaction are collected in a cooled condenser attached to the end of the reactor and the products are analyzed using a gas chromatograph. The products were identified using gas chromatography or mass spectroscopy and thereafter, the products are quantitatively analyzed using gas chromatography. The results are summarized in Table 1, Table 2 and Table 3.

TABLE 1

| Catalyst 1 | Temperature (° C.) | Benzene:Ethylene (Mole Ratio) | Benzene Conversion (%) | EthylBenzene Selectivity (%) |
|---|---|---|---|---|
| 1 | 400 | 1:1 | 59.42 | 83.20 |
| 2 | 450 | 1:1 | 56.84 | 86.78 |
| 3 | 400 | 3:1 | 45.24 | 85.26 |
| 4 | 450 | 3:1 | 37.33 | 95.40 |
| 5 | 400 | 6:1 | 26.13 | 89.37 |
| 6 | 450 | 6:1 | 22.35 | 96.03 |

TABLE 2

| Catalyst 2 | Temperature (° C.) | Benzene:Ethylene = Mole Ratio | Benzene Conversion (%) | EthylBenzene Selectivity (%) |
|---|---|---|---|---|
| 1 | 400 | 1:1 | 60.52 | 81.50 |
| 2 | 450 | 1:1 | 57.91 | 85.98 |
| 3 | 400 | 3:1 | 47.12 | 82.97 |
| 4 | 450 | 3:1 | 39.32 | 94.85 |
| 5 | 400 | 6:1 | 28.22 | 87.28 |
| 6 | 450 | 6:1 | 24.46 | 95.89 |

TABLE 3

| Catalyst 3 | Temperature (° C.) | Benzene:Ethylene = Mole Ratio | Benzene Conversion (%) | EthylBenzene Selectivity (%) |
|---|---|---|---|---|
| 1 | 400 | 1:1 | 62.61 | 80.54 |
| 2 | 450 | 1:1 | 58.84 | 84.38 |
| 3 | 400 | 3:1 | 48.35 | 82.17 |
| 4 | 450 | 3:1 | 40.42 | 94.10 |
| 5 | 400 | 6:1 | 30.22 | 86.21 |
| 6 | 450 | 6:1 | 26.46 | 94.08 |

Various embodiments of the invention provide an efficient method for preparing ethylbenzene. The invention also provides a method of preparing a zeolite catalyst that is used to prepare ethylbenzene in one cycle process. The method for preparing ethylbenzene with both unmodified and modified zeolite catalysts provides ethylbenzene as the main product and by-products such as diethylbenzene (ortho, meta and para) isomers as minor products. The by-products are less than 10%. In an ethylation reaction of the invention, there is no formation of other ethylated benzene such as, but not limited to, triethylbenzene isomers (1,2,4-triethylbenzene; 1,2,3-triethylbenzene and 1,3,5-triethylbenzene); tetraethylbenzene isomers (1,2,3,4-tetraethylbenzene; 1,2,3,5-tetraethylbenzene; and 1,2,4,5-tetraethylbenzene); 1,2,3,4,5-pentaethylbenzene; 1,2,3,4,5,6-hexaethylbenzene or higher molecular weight alkylaromatic compounds. The selectivity of ethylbenzene in one cycle ethylation reaction ranges between 81% and 96% and the conversion of benzene ranges between 22% and 63%. The unmodified and modified zeolites are active as catalysts for the one cycle gas phase ethylation of benzene. The unmodified and modified zeolites are also selective to ethylbenzene with less formation of by-products. Thus, the method of alkylation of benzene with unmodified or modified zeolite catalyst is suitable for one cycle alkylation of benzene with ethylene, isomerization of ethylated benzene, transalkylation of diethylbenzene and triethylbenzene isomers with benzene and disproportionation of ethylated benzenes process in a same reactor.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:
1. A method of alkylating benzene in a one cycle process in the presence of a catalyst within a single fixed bed reactor without recycling byproducts to an additional reactor or a transalkylator, the method comprising:

charging benzene and ethylene gas feedstock to an alkylation zone in the fixed bed reactor and heating the benzene and ethylene gas feedstock;

contacting the heated benzene and the ethylene gas feedstock in the alkylation zone with the fixed bed reactor;

adding the catalyst in a catalyst zone of the fixed bed reactor; and conducting the alkylating benzene with ethylene, the alkylating is carried out in a continuous gas phase in the presence of a diluent of inert gas of at least one of nitrogen, helium, or argon with a flow rate of less than 4.5 milliliters/minute with a feed weight hourly space velocity (WHSV) based on the ethylene gas feedstock from 0.1 $hr^{-1}$ to 400 $hr^{-1}$, wherein the catalyst is a modified zeolite catalyst comprising (i) zeolite with a weight percent (wt %) ratio of silica to alumina ranging between 5 wt % to 95 wt % of silica and 95 wt % to 5 wt % alumina, (ii) kaolinite and (iii) a binder, wherein the zeolite is modified with at least one metal oxide of the Lanthanide series of the Periodic Table, and wherein the catalyst has an ethylbenzene selectivity of 81%-96%.

2. The method of claim 1, wherein a molar ratio of benzene to ethylene in the benzene and ethylene gas feedstock is 1:6 to 15:1.

3. The method of claim 1, wherein the alkylating benzene is carried out in one cycle continuous gas phase using the fixed bed reactor in a bench top pilot plant.

4. The method of claim 1, wherein the alkylating benzene is carried out under a pressure range of from 1.0 bar to 20 bar.

5. The method of claim 1, wherein the alkylating benzene is carried out under a temperature range of from 100° C. to 500° C.

* * * * *